US00PP33100P2

(12) United States Plant Patent
Van Dijk

(10) Patent No.: US PP33,100 P2
(45) Date of Patent: May 25, 2021

(54) ***ANTHURIUM* PLANT NAMED 'ANTHFETBA'**

(50) Latin Name: ***Anthurium andraeanum* L.**
Varietal Denomination: ANTHFETBA

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/020,977

(22) Filed: Sep. 15, 2020

(51) Int. Cl.
*A01H 5/02* (2018.01)
*A01H 6/10* (2018.01)

(52) U.S. Cl.
USPC ..... Plt./365
CPC ..... *A01H 6/10* (2018.05)

(58) Field of Classification Search
USPC ..... Plt./365, 367, 368, 369
CPC ..... A01H 5/02
See application file for complete search history.

*Primary Examiner* — Kent L Bell

(74) *Attorney, Agent, or Firm* — Jondle & Associates, P.C.

(57) ABSTRACT

A new *Anthurium* plant named 'ANTHFETBA' particularly distinguished by having shiny and weakly blistered, reddish-pink, orbicular-cordate, and durable spathes that retain the original color for a very long period of time, shiny, dark green and narrowly cordate, durable leaves, pink spadices with orange tips, early and rich flowering continuously throughout the year, and a plant height of 26.0 cm to 31.0 cm is disclosed.

3 Drawing Sheets

Genus and species: *Anthurium andraeanum* L.
Variety denomination: 'ANTHFETBA'.

BACKGROUND OF THE NEW PLANT

The present invention comprises a new and distinct variety of *Anthurium*, botanically known as *Anthurium andraeanum* L., and hereinafter referred to by the variety name 'ANTHFETBA'. The new *Anthurium* plant is a product of a planned breeding program conducted by the inventor in Bleiswijk, the Netherlands. The objective of this breeding program was to create a new plant with a height of 26.0 cm to 31.0 cm having shiny, weakly blistered, reddish-pink, orbicular-cordate, and durable spathes.

The new variety originated from a cross-pollination made in August 2010 in Bleiswijk, the Netherlands. The female parent was a pink *Anthurium* pot plant designated '20441-06' (unpatented), and the male parent was a pink *Anthurium* pot plant designated 'ANTHDATAM' (U.S. Plant Pat. No. 27,699).

A single plant was selected from the progeny of the stated cross in July 2012. Asexual reproduction of the new variety by tissue culture in 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 1, 2018 (Application no. 2018/2886), by Applicant who obtained the subject matter disclosed directly from the inventor. 'ANTHFETBA' has not been made publicly available or sold anywhere in the world prior to the effective filing date of this application with the exception of sales or disclosures made one year or less before the effective filing date of this claimed invention by Applicant who obtained 'ANTHFETBA' directly from the inventor.

SUMMARY OF THE INVENTION

The following are the most outstanding and distinguishing characteristics of this new variety when grown under normal horticultural practices in Bleiswijk, the Netherlands:

1) Shiny, weakly blistered, reddish-pink, orbicular-cordate spathes;
2) Pink spadices with orange tips;
3) Dark green, shiny, narrowly cordate leaves; and
4) Spathes are positioned slightly above the leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 34-week-old plant grown in a greenhouse in Bleiswijk, the Netherlands, in July 2020. Colors in the photographs may differ from the color values cited in the detailed botanical description, which accurately describe the actual colors of the new variety.

DESCRIPTION OF THE NEW VARIETY

Figure 1:
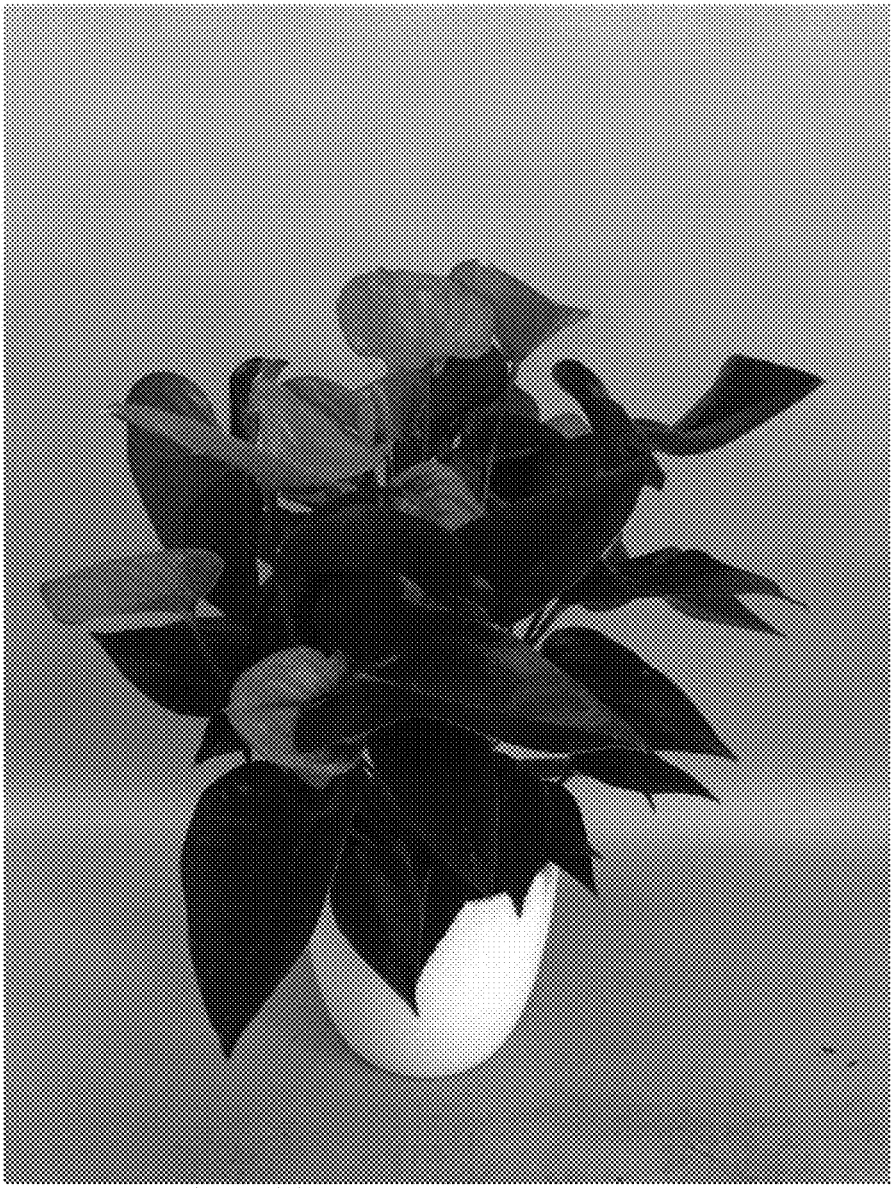
FIG. 1 shows the overall plant habit, including blooms and foliage.
Figure 2:
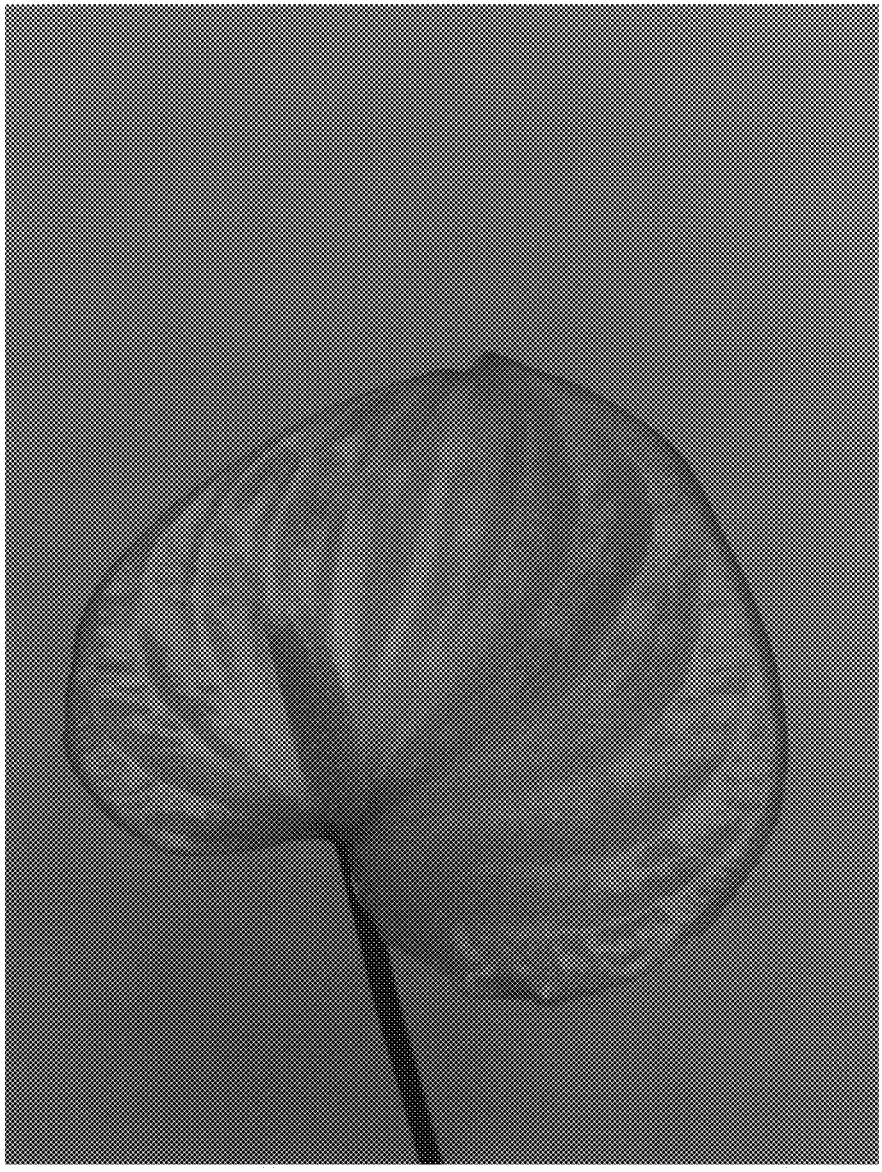
FIG. 2 shows a close-up of the mature spathe.
Figure 3:
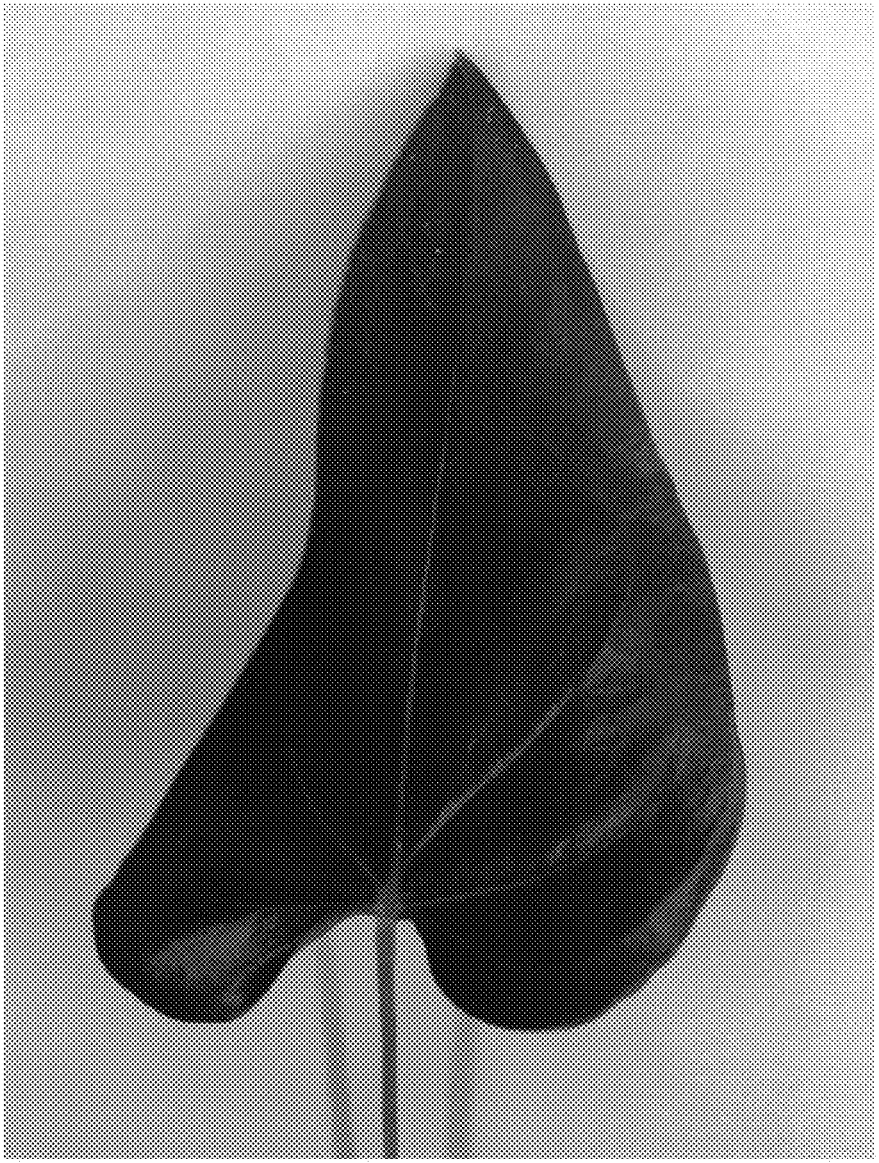
FIG. 3 shows a close-up of the upper leaf blade surface.

The following detailed description sets forth the distinctive characteristics of 'ANTHFETBA'. The data which define these characteristics were collected from asexual reproductions carried out in Bleiswijk, the Netherlands. The plant history was taken on 34-week-old plants which were planted from tissue culture in 12-centimeter (diameter) pots and grown in a glass greenhouse between 19° C. and 24° C. Observations were made in July 2020. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHFETBA'.

Parentage:

*Female parent*.—*Anthurium* plant '20441-06' (unpatented).

*Male parent*.—*Anthurium* plant 'ANTHDATAM' (U.S. Plant Pat. No. 27,699).

Plant:

*Propagation*.—Tissue culture.

*Root description*.—Fleshy-creamy (RHS 155A) colored roots with small hairy lateral roots having yellow (RHS 7A) colored root tips.

*Time to produce a finished flowering plant*.—32 to 36 weeks after planting in a 12-cm (diameter) pot.

*Growth habit*.—Upright.

*Height* (*measured from soil, including inflorescence*).—26.0 cm to 31.0 cm.

*Width* (*measured from leaf tips*).—27.0 cm to 32.0 cm.

Leaves:

*Immature leaves*.—Length: 12.0 cm to 15.0 cm. Width: 7.0 cm to 9.0 cm. Color: Upper surface: RHS 146A. Lower surface: RHS 146B. Texture (both upper and lower surfaces): Leathery.

*Mature leaves*.—Length (fully expanded): 15.0 cm to 17.0 cm. Width: 9.0 cm to 11.0 cm. Shape: Narrowly cordate. Apex: Abruptly acuminate. Base: Cordate. Leaf blade angle with the petiole: Between 120 degrees and 140 degrees. Leaf margin: Entire. Color: Upper surface: RHS 147A. Lower surface: RHS 146B. Texture (both upper and lower surfaces): Leathery, leathery, and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Present. Arrangement: Leaf blade has two lobes extending past the petiole. The lobes are non-touching. Length of lobes of mature leaf blades: 1.0 cm to 1.5 cm. Width of lobes of mature leaf blades: 3.0 cm to 4.0 cm. Distance from petiole/leaf junction to highest point on lobes of mature leaf: 3.0 cm to 4.0 cm.

*Petiole*.—Cross-section: Round. Diameter: 0.3 cm to 0.4 cm. Length: 15.0 cm to 18.0 cm for a mature leaf size. Color: Mature leaf: RHS 144A. Immature leaf: RHS 144B. Cataphyll color surrounding the petiole: Outside: RHS 145C. Inside: RHS 145D.

*Geniculum*.—Length: 1.5 cm to 2.5 cm. Width: 0.3 cm to 0.5 cm. Color: RHS 144A.

Inflorescence:

*Arrangement*.—Single.

*Flowering habit* (*length of flowering season*).—Continuous.

*Number of inflorescences per plant*.—7 to 9.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully opened, the peduncle elongates.

*Arrangement*.—Spathe angle with the peduncle is between 95 degrees and 115 degrees; the spathe stands on a wiry peduncle about 2.0 cm to 5.0 cm above the foliage.

*Shape*.—Orbicular cordate.

*Apex*.—Mucronate.

*Base*.—Cordate.

*Texture*.—Shiny and weakly blistered.

*Margin*.—Undulated.

*Size*.—Length: 8.0 cm to 8.5 cm. Width: 7.5 cm to 8.0 cm.

*Lobes*.—Present. Arrangement: The spathe has two lobes extending past the peduncle. The lobes are non-touching. Length: 0.5 cm to 1.0 cm. Width: 2.5 cm to 3.0 cm.

*Color*.—Just fully open: Upper surface: RHS 52A. Lower surface: RHS 52C. This reddish-pink color remains for a very long period, at least more than 30 weeks after opening. The spathe turns green after some weeks.

Peduncle:

*Shape*.—Erect.

*Cross-section*.—Round.

*Length*.—20.0 cm to 23.0 cm.

*Diameter*.—0.3 cm to 0.4 cm.

*Color*.—RHS 144B.

Flowering time:

*General*.—One small, rooted, untreated tissue culture plant of 8.0 cm tall will flower, depending on the season, after 32 to 36 weeks and 7 to 8 blossoms appear. More blossoms appear after some additional weeks so that a full flowering and commercial plant will have 8 to 9 reddish-pink spathes. Smaller blossoms may occur on immature plants.

Spadix:

*Size*.—Length: 2.5 cm to 3.0 cm (depending on flower size). Width (at apex): 0.4 cm to 0.5 cm. Width (at base): 0.5 cm to 0.6 cm.

*Shape*.—Columnar.

*Angle of spadix tip with peduncle*.—160 degrees to 180 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 33B. Mature: RHS 51B. Ages to: RHS 152A with pistils color RHS 175C.

Flowers:

*Quantity per spadix*.—80 to 130.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 51D.

Reproductive organs:

*Stamens*.—Not visible.

*Pollen amount*.—Absent.

*Pistil*.—Quantity: Many. Length: Less than 0.01 cm. Color: RHS 51D.

*Style*.—Not observed to date.

*Stigma*.—Shape: Ovoid. Diameter: Less than 0.01 cm. Color: RHS 51D.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'ANTHFETBA' differs from the female parent plant '20441-06' (unpatented) in that 'ANTHFETBA' has a straight spathe shape in cross section of the middle zone and spadices that are pink at the base, whereas '20441-06' has a concave spathe shape in cross section of the middle zone and spadices that are white at the base.

'ANTHFETBA' differs from the male parent plant 'ANTHDATAM' (U.S. Plant Pat. No. 27,699) in that 'ANTHFETBA' has orbicular-cordate spathes and spadices that are pink at the base, whereas 'ANTHDATAM' has cordate spathes and spadices that are purplish-red at the base.

'ANTHFETBA' differs from similar commercial variety 'ANTHDINWAQ' (U.S. Plant Pat. No. 26,048) in that 'ANTHFETBA' has a straight spathe shape in cross section of the middle zone and spathes that are positioned slightly above the foliage, whereas 'ANTHDINWAQ' has a concave spathe shape in cross section of the middle zone and spathes that are positioned far above the foliage. Additionally, 'ANTHFETBA' has wider spathes than 'ANTUDINWAQ'.

'ANTHFETBA' differs from similar commercial variety 'ANTHOSZMO' (U.S. Plant Pat. No. 31,416) in that 'ANTHFETBA' has a straight spathe shape in cross section of the middle zone and narrowly cordate leaves, whereas 'ANTHOSZMO' has a concave spathe shape in cross section of the middle zone and deltoid leaves. Additionally, 'ANTHFETBA' has wider spathes than 'ANTHOSZMO'.

I claim:

1. A new and distinct variety of *Anthurium* plant named 'ANTHFETBA', substantially as illustrated and described herein.

* * * * *